United States Patent
Aquino

(10) Patent No.: US 11,998,217 B2
(45) Date of Patent: Jun. 4, 2024

(54) COMPRESSIVE CRYO-HEMOSTATIC DEVICE

(71) Applicant: Alexandre Arantes Aquino, Santo André (BR)

(72) Inventor: Alexandre Arantes Aquino, Santo André (BR)

(73) Assignees: Alexandre Arantes Aquino (BR); Fernanda Moreiralopes (BR); Ulisses Chernichenco De Oliveira (BR)

( * ) Notice: Subject to any disclaimer, the term of this patent is extended or adjusted under 35 U.S.C. 154(b) by 738 days.

(21) Appl. No.: 17/263,151

(22) PCT Filed: Jul. 23, 2019

(86) PCT No.: PCT/BR2019/050291
§ 371 (c)(1),
(2) Date: Jan. 25, 2021

(87) PCT Pub. No.: WO2020/019046
PCT Pub. Date: Jan. 30, 2020

(65) Prior Publication Data
US 2021/0161540 A1    Jun. 3, 2021

(30) Foreign Application Priority Data
Jul. 26, 2018 (BR) .................. 10 2018 015256 4

(51) Int. Cl.
*A61B 17/132* (2006.01)
*A61B 17/12* (2006.01)
*A61F 7/10* (2006.01)
*A61F 7/02* (2006.01)

(52) U.S. Cl.
CPC .......... *A61B 17/1325* (2013.01); *A61F 7/103* (2013.01); *A61B 2017/12004* (2013.01); *A61F 2007/0231* (2013.01); *A61F 2007/0268* (2013.01); *A61F 2007/0282* (2013.01)

(58) Field of Classification Search
CPC .............. A61F 7/103; A61F 2007/0282; A61F 2007/0268; A61F 2007/0231; A61B 2017/12004; A61B 17/1325
See application file for complete search history.

(56) References Cited

U.S. PATENT DOCUMENTS

2014/0012120 A1* 1/2014 Cohen ................ A61B 5/02042
                                                    600/371
2015/0018869 A1* 1/2015 Benz .................... A61B 17/135
                                                    606/203

(Continued)

*Primary Examiner* — Jing Rui Ou

(57) ABSTRACT

This is a device, belonging to the medical and hospital artifacts industry, developed to accelerate the hemostatic process for patients undergoing radial punctures, partially compressing the artery subjected to treatment; said cryo-hemostatic device is essentially presented in the form of a wristband (1), providing end bands (2) providing velcro-based closing, interconnected by an intermediate band (3) below which a first cryogenic reservoir pad is located (4), which can be filled with a saline substance by the action of a syringe connected to the first connection nipple (5) attached to the first tube (6), flanked by the second external reservoir pad (7), also provided with a second connection nipple (8), attached to the second tube (9).

1 Claim, 2 Drawing Sheets

(56) References Cited

U.S. PATENT DOCUMENTS

2016/0174952 A1\* 6/2016 Shah ................. A61B 17/0057
                                                    606/213
2017/0035439 A1\* 2/2017 Pancholy ............ A61B 17/135
2018/0199947 A1\* 7/2018 Benz ................. A61B 17/1325

\* cited by examiner

COMPRESSIVE CRYO-HEMOSTATIC DEVICE

This is intended to describe and provide a visual presentation of a compressive cryo-hemostatic device, which is included in the hospital and medical artifacts industry.

More precisely, said artifact has been conceived, designed and developed to provide, in the field of interventional medicine, acceleration of the hemostatic process for patients who have undergone radial punctures, whose method is most commonly used in cardiac catheterization and coronary angioplasty procedures, partially compressing the artery subjected to the insertion of a catheter through a reservoir pad containing a plate with cryogenic material, based on polymer and non-toxic treated water.

As known mainly by professionals and other individuals who work in the industry, hemostasis basically refers to a variety of mechanisms and procedures oriented to keep blood flowing within the vessels, in order to avoid coagulation (thrombosis) or overflow (hemorrhage) thereof.

Thus, prior to delving into the unique inventive merits of the subject matter of the patent application in question, and to assist in locating the state of the art related to the subject matter disclosed herein, certain documents referring to similar solutions may be quoted—which, nevertheless, fail to reach the innovative concepts introduced and described herein, and illustrated in the figures included in the present application. Otherwise, let's see:

BR102013014339-1, relating to an improved hemostatic clamp having a first segment provided with a pair of longitudinal ribs laid out between the free end portion of the first segment and the proximity of the hinge zone; said longitudinal ribs are spaced apart by a longitudinal groove, and their crest features indentations laid out with a pyramidal trunk profile interleaved with transverse recesses; the second segment features two flat-profiled longitudinal grooves aligned with the pair of longitudinal grooves laid out in the first segment; the longitudinal grooves are interspaced with a longitudinal groove provided with indentations with pyramidal trunk profile at the crest, interspersed by transverse recesses; said longitudinal rib is aligned with the longitudinal groove of the first segment, so that the indentations of the crest prevent the vessel displacement in the distal and proximal directions, and promote the full closure of the vessel;

MU 9100069-6, which relates to a hemostatic device featuring an air passage duct, and includes a band adapted for winding around a patient's limb where bleeding needs to be stopped; a curved plate; a surface fastener to secure the band in a state wound onto the limb; a balloon connected to the band, which inflates when a fluid is introduced therein; a marker to position the balloon at the site where the bleeding needs to be stopped, wherein air cavities are also provided in the band, the surface fastener, and the curved plate;

MU 9100127-7, is a syringe for a hemostatic device, including means to hold a joint in a designated position or induce a user to hold the joint being provided with a drum, a sliding contact joint within said drum, a pusher inserted through an aperture of a base end of the drum, and that operates the joint to render it movable, and a rod-shaped limiter provided on the inner side of the drum, configured to protrude through the aperture of the base end of said drum towards the proximal end, and integrated thereto, where the pusher is directed in the state that the distal end surface of the joint interfaces with the proximal end of the rod-shaped stop, until the surface of the proximal end of said joint interfaces with the bottom portion of the drum, so that an exact amount of air can be infected into the hemostatic device;

P1 0707104-3, is an inert, non-reactive hemostatic agent delivery system capable of forming a stable clot when applied to a bleeding wound, also including a delivery kit to structure and facilitate the delivery of the hemostatic agent close to the bleeding site, structured to contain the hemostatic agent through the release member, which is arranged in a cooperative relationship with the support member containing the amount of the hemostatic agent, whose release member is made of a soluble material that will at least partially dissolve and release the hemostatic agent on the arrangement close to the bleeding site; said assembly further includes a crank member structured to make dispensing the hemostatic agent at the bleeding site easier.

With regard to the model introduced herein, the process occurs with the reservoir pad that contains the chilled plate being involved onto the limb where the puncture has been made, and the catheter insertion being fastened with a velcro or similar means, anatomically accommodating to the patient.

Then, said reservoir pad is filled through a syringe with a saline substance into a non-return valve system, rapidly cooling in contact with the chilled plate, insufflating and generating pressure enough to withdraw the catheter and stagnate the blood until the frozen substance performs the whole hemostasis process.

This technology allows partially compressing an artery, leaving another artery free to irrigate and oxygenate the limb, and the direct contact with the low temperature reached by using a cryogenic substance provides a number of benefits for both patients and the hospital facilities where such procedures are performed, which include:

post-procedure vasoconstriction, which allow using catheters of a wider caliber during the test;

accelerated hemostasis due to the low temperature, reducing the patients' time of exposure to the hospital environment, with faster discharges, also providing conditions for the facilities to increase the number of visits;

decreased nerve conduction, minimizing pain and prolonging the anesthetic feel;

mitigates the inflammatory processes, also reducing edema;

decreases muscle spasms and their consequent pain/discomfort;

stimulates relaxation;

allows early mobilization due to pain reduction;

improves the motion range by acting on the coagulation cascade.

After application within the period indicated by the attending healthcare professionals, as required to complete the hemostatic process, the pressing reservoir pad starts being emptied, causing the normal blood flow to gradually normalize, drastically reducing hospitalization time, providing benefits to patients, family members and/or companions alike, as well as the hospital unit, which can extend its services to those who need them most.

Its key differentiator is the moment of withdrawal of the cryogenic substance from the compressing reservoir pad through a conventional syringe, which, after a certain time, matches the body temperature, whose substance is aspirated so as to be directed to and stored in a second reservoir pad attached to the device, thus avoiding that the professional handling has to leave the bedside to discard it, or that disposal containers specific for this purpose are provided in advance.

From a constructive perspective, said cryo-hemostatic device is provided basically in the form of a wristband, with end bands featuring velcro, interconnected by an intermediate band below which a first cryogenic reservoir pad is located, filled with a saline substance through the action of a syringe connected to the first connection nipple attached to the first tube, flanked by the second external reservoir pad, also provided with a second connection nipple attached to the second tube, thereby providing the hemostatic process.

After said process is completed, the cryogenic substance can be removed from the first reservoir pad and stored in the second external reservoir pad, also provided with a second connection nipple with a return valve, attached to its second tube, greatly facilitating the tasks of the caregivers in charge.

In order to further assist in the understanding of the subject mailer of the present patent application, illustrations are appended, through which reference will be made together with the following description, so that:

Figure 1:
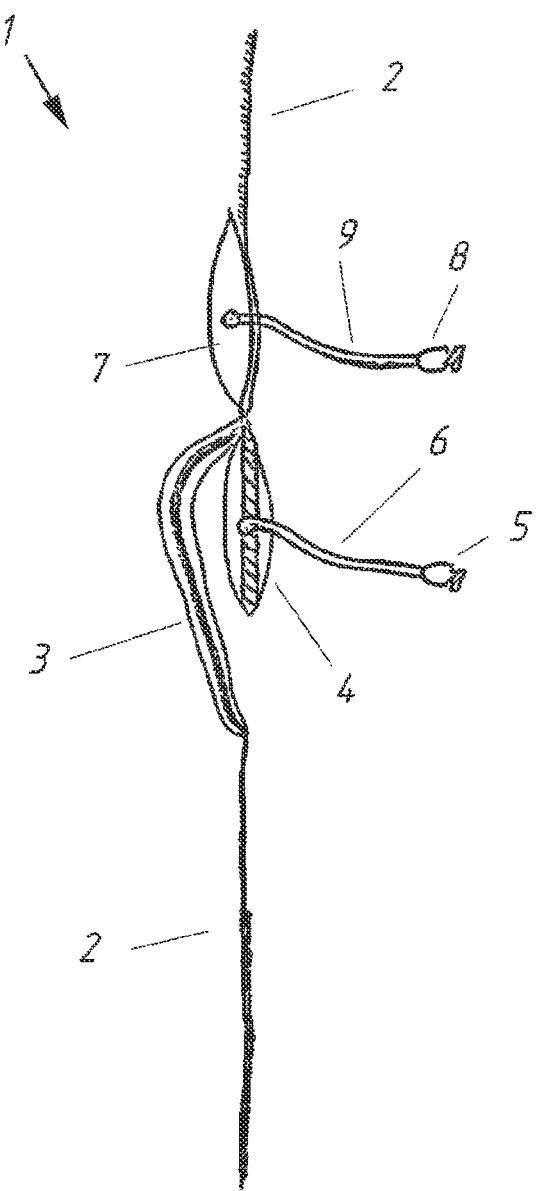
FIG. 1 shows the cryo-hemostatic device in question, in a side view.
Figure 2:
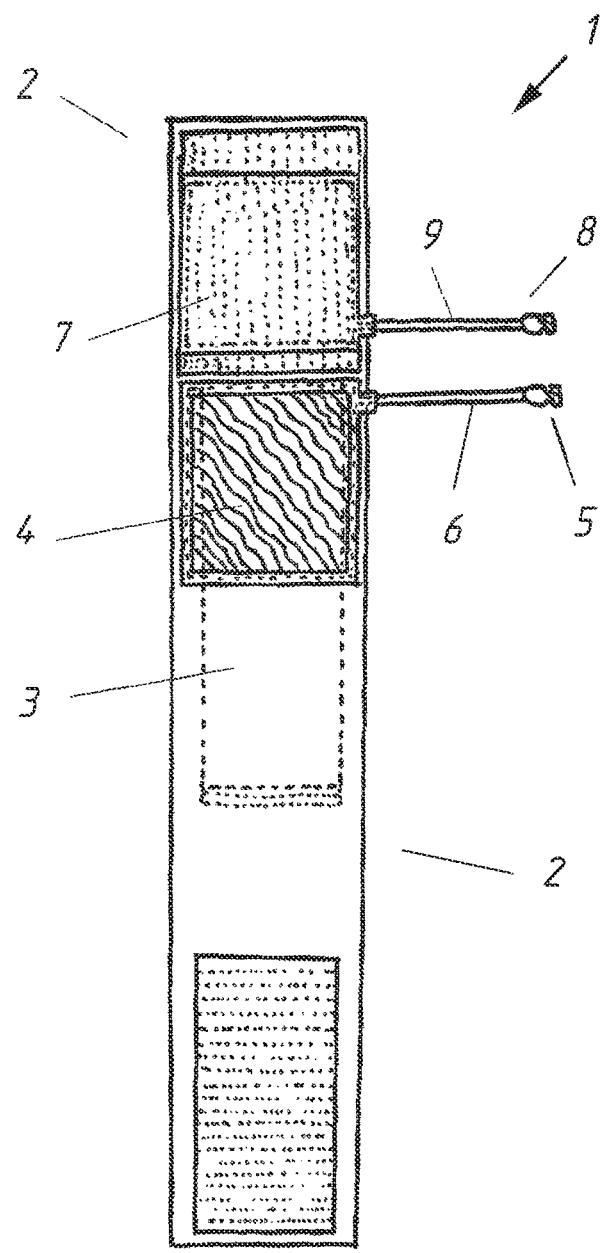
FIG. 2 shows it as a top plan.

Considering said Figures, taken together with the following description, the present patent application is for a cryo-hemostatic compressive device, belonging to the medical and hospital artifacts industry, developed to accelerate the hemostatic process for patients undergoing radial punctures, partially compressing the artery subjected to treatment; said cryo-hemostatic device is essentially presented in the form of a wristband (1), providing end bands (2) providing velcro-based closing, interconnected by an intermediate band (3) below which a first cryogenic reservoir pad is located (4), which can be filled with a saline substance by the action of a syringe connected to the first connection nipple (5) attached to the first tube (6), flanked by the second external reservoir pad (7), also provided with a second connection nipple (8), attached to the second tube (9).

It should be noted that the cryo-hemostatic device disclosed herein may have its features and technical capabilities modified, given the possibility of version updates, maintaining or even improving the performance achieved, including with regard to the use of different raw materials and dimensions, without moving away from the spirit and scope of the present explanation, therefore embedding highly convenient innovations, whose development brought better solutions for its relevant use, achieving the intended objectives and meeting the essential requirements of novelty, inventive activity and industrial application that fully warrant the protection sought.

What is claimed is:

1. A compressive cryo-hemostatic device comprising:
    a wristband (1) with end bands (2) provided with Velcro on opposite ends operable to secure the device around a wrist of a user;
    an intermediate band (3) provided between the end bands (2);
    a first cryogenic reservoir pad (4) configured to be filled with a saline substance through a syringe via a first connection nipple (5) attached to a first tube (6), wherein the syringe is configured to be operably connected to the first connection nipple (5); and
    a second external reservoir pad (7) provided with a second connection nipple (8) attached to a second tube (9), wherein,
        the first cryogenic reservoir pad (4) is disposed adjacent to the second external reservoir pad (7);
        the first cryogenic reservoir pad (4) is isolated from the second external reservoir pad (7);
        one end of the intermediate band (3) is connected to a portion between the first cryogenic reservoir pad (4) and the second external reservoir pad (7), and another end of the intermediate band (3) is connected to at least one of the end bands (2) such that the first cryogenic reservoir pad (4) is configured to be disposed below the intermediate band (3) thereby being exposed to the wrist of the user when the device is secured to the wrist of the user; and
        the second external reservoir pad (7) is disposed over at least a portion of the end bands (2) such that the second external reservoir pad (7) remain unexposed to the wrist of the user when the device is secured to the wrist of the user.

\* \* \* \* \*